Figure 1:
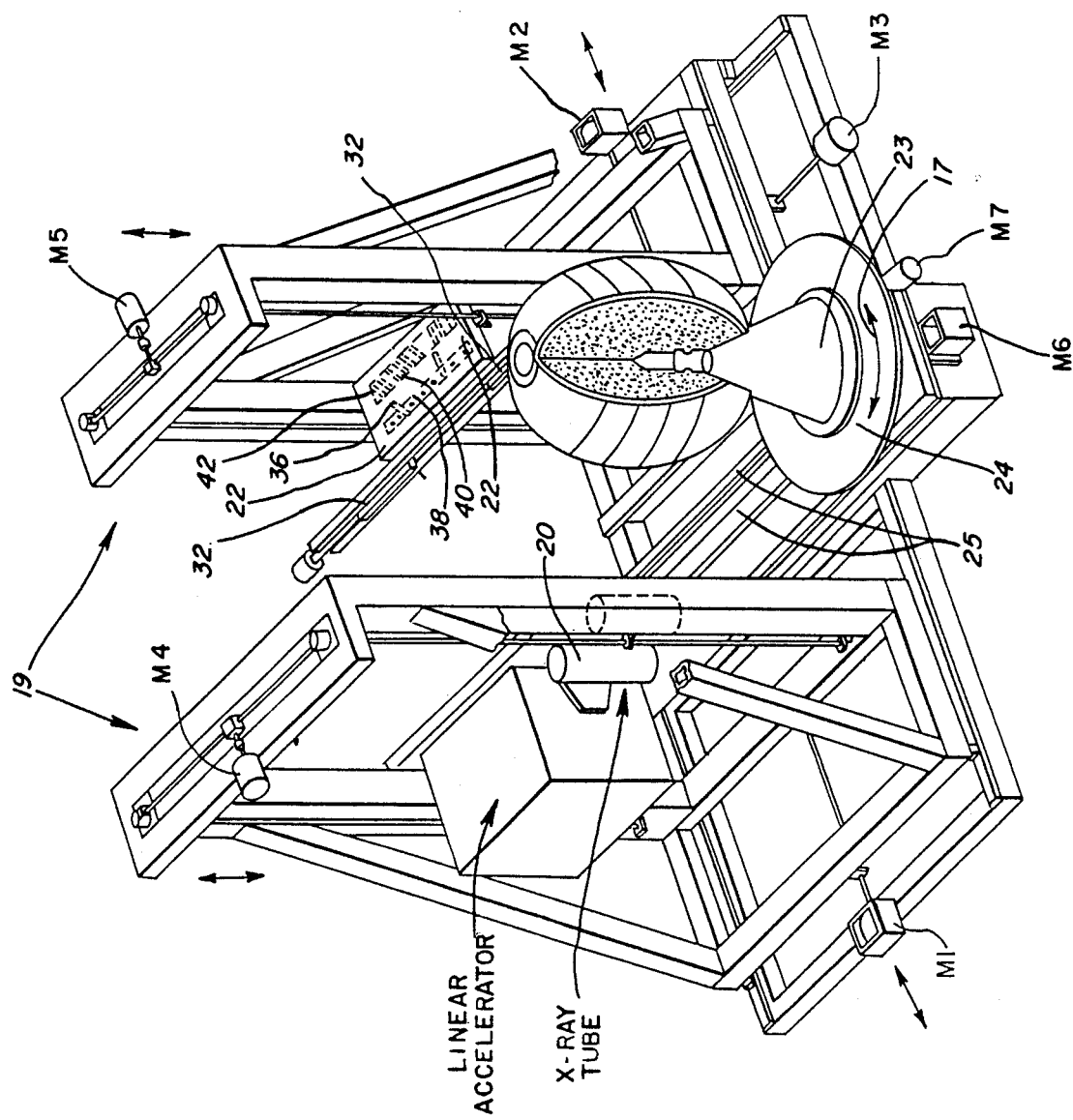

United States Patent [19]

Bernardi et al.

[11] Patent Number: 4,984,257
[45] Date of Patent: Jan. 8, 1991

[54] AUTOMATIC DYNAMIC FOCUSING FOR COMPUTED TOMOGRAPHY

[75] Inventors: Richard T. Bernardi; John F. Moore, both of Lincolnshire, Ill.

[73] Assignee: Bio-Imaging Research, Inc., Lincolnshire, Ill.

[21] Appl. No.: 496,679

[22] Filed: Mar. 21, 1990

Related U.S. Application Data

[63] Continuation of Ser. No. 122,797, Nov. 19, 1987.

[51] Int. Cl.$^5$ ............................................. G01N 23/00
[52] U.S. Cl. ........................................ 378/13; 378/19; 378/146
[58] Field of Search ............................ 378/13, 19, 146

[56] References Cited

U.S. PATENT DOCUMENTS

| | | | |
|---|---|---|---|
| 4,084,094 | 4/1978 | Troggatt | 378/13 |
| 4,856,041 | 8/1989 | Klein et al. | 378/19 |
| 4,928,297 | 5/1990 | Tsutsui et al. | 378/146 |

*Primary Examiner*—Craig E. Church
*Attorney, Agent, or Firm*—Laff, Whitesel, Conte & Saret

[57] ABSTRACT

A dynamic focusing device is provided for an X-ray scanner, the device comprising at least one detector module located in a position to receive, be illuminated by, and respond to X-rays. A source of X-rays is movable toward or away from the detector module. The module comprises a plurality of crystals each having a scintillation surface located in a common plane, with a plurality of septa separating the crystals. The septa have a height which is upstanding above the surfaces of the crystals far enough to reduce lateral X-ray scatter and to cast a shadow upon the surfaces of the crystals responsive to an illumination thereof from said X-ray source. The invention dynamically positions the detector module relative to the distance between the detector module and the source of X-rays in order to reduce substantially to a minimum any shadow in the X-rays cast by the septa upon the surfaces of the crystals.

10 Claims, 3 Drawing Sheets

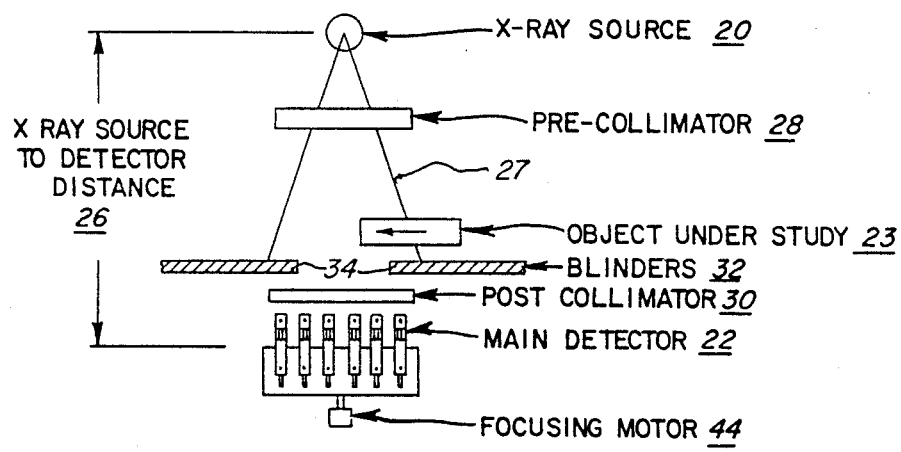
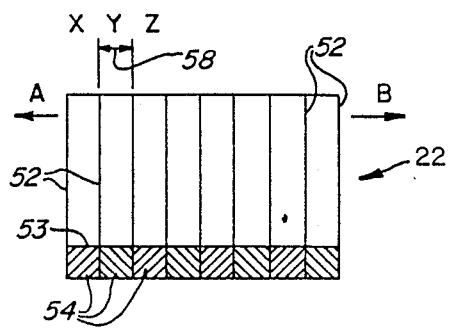
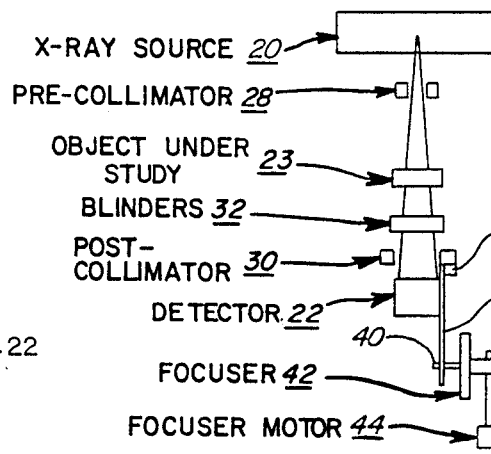
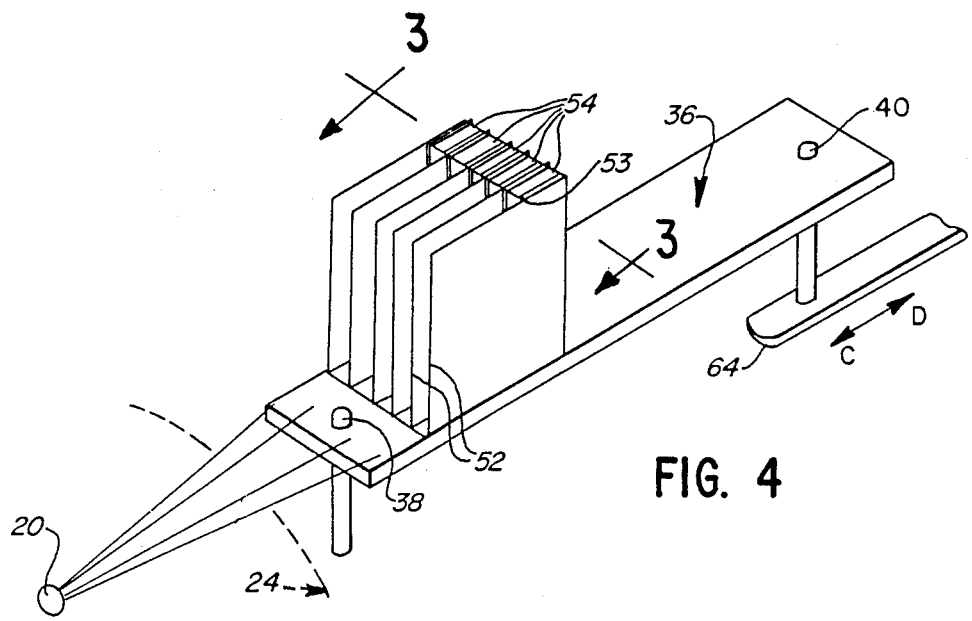

AUTOMATIC DYNAMIC FOCUSING FOR COMPUTED TOMOGRAPHY

This application is a continuation of prior application Ser. No. 07/122,797, filed Nov. 19, 1987.

This invention relates to computed tomography (commonly called "CAT or CT scanning") and more particularly to means and methods for dynamically focusing or directing detectors for CAT scanners directly toward a source of X-rays.

Reference is made to my simultaneously filed and copending patent applications Ser. Nos. 07/122,909, filed Nov. 19, 1987, entitled "Cam-Controlled Automatic Dynamic Focusing For Computed Tomography", now U.S. Pat. No. 4,872,191, and No. 07/122,905 entitled "Blinder for CAT Scanner", now abandoned, a continuation-in-part of which is now U.S. Pat. No. 4,891,833, for a further description of some of the elements disclosed herein.

A single-channel, discrete, solid-state X-ray detector has an individual scintillation crystal mounted on a dedicated silicon photodiode. A multiplicity of such detectors may be joined together for use as a multichannel module. Such a module may be fabricated as a one-dimensional linear array with a common multichannel silicon carrier and with individual scintillation crystals separated from each other by upstanding collimating walls or septa. The linear array of detectors may be abutted against each other in a straight line configuration; or, in the alternative, they may be arranged in a curvilinear configuration so that each module is radially focused on (directed toward) a common X-ray source. Imaging applications for either the straight or curvilinear arrays are found in digital radiography and in computed tomography ("CAT scanning").

The collimating walls or septa are positioned between the crystals to give channel-to-channel crystal separation, in order to improve X-ray scatter rejection (i.e. to prevent X-rays which are scattered laterally across the surfaces of the crystals from causing false readings). The septa are somewhat similar to the dividers along one row of an egg crate or ice cube tray. The detector crystals are buried deep within and at the bottom of the space between the dividers.

The best scatter rejection is achieved by use of septa made from an excellent X-ray attenuator material, such as tungsten, and by increasing the height of the septa above the scintillation surface of the crystal. Such a height increase produces an increase in scatter rejection, since the rejection is proportional to the ratio of the septa height above the crystal surface, to the scintillator width.

However, polar response, the ability of a detector to accept direct (non-scattered) x-rays from a source which is not located directly on the focal axis of the detector, is also a function of the ratio of the height of the septa to the active width of the individual crystals, and is inversely proportional to septa height. Thus, an increase in polar response requires lower septa for a given crystal width, but such a lowering of the septa increases the susceptibility to false readings from X-ray scattering. This forces a trade-off between polar response and scatter rejection.

Therefore, it becomes important to control the X-ray angle of incidence illuminating the surface of the scintillation crystal. An X-ray source is somewhat like a floodlight illuminating the surface of the array. The septa rise to a height which casts shadows upon the surfaces of the crystals, unless the entire array is pointed directly toward the source. When the septa cast shadows on the surfaces of the crystals, it greatly reduces the efficiency of the entire array by reducing the scintillation response of the crystals. This invention is designed to either eliminate or minimize such shadows by continuously and dynamically directing (focussing) the array toward the X-ray source throughout an entire CAT scan.

In the past, digital radiography and computed tomography systems have had a fixed X-ray source-to-detector distance which has only required a fixed focus. Therefore, once the detectors were properly directed, there was no need to redirect them. Recently, however, CAT scanners have varied the source-to-detector distance for providing optimal CAT scanning over a wide variety of object sizes, which is especially important for industrial uses. The newer systems are also designed to decrease X-ray scatter, and they thereby reduce the polar response of the detector because they employ tall tungsten septa between the scintillation crystals. In such an environment the invention must dynamically focus the arrays of solid-state X-ray detectors in response to a decrease in detector polar response resulting from a variation in source-to-detector distance. That is, the invention must always point the detector array in a direction such that the septa cast a minimum x-ray shadow.

In keeping with an aspect of the invention, a CAT scanner system is provided for dynamically X-raying an object, such as an industrial product. An X-ray source is directed to illuminate a given area, which is remote from the X-ray source by a variable distance. A detector comprises a plurality of crystals separated by septa for collecting X-rays falling on a surface in the given area. The septa produce shadows which increase or decrease as a function of the angle of incidence of X-rays illuminating the surface of the crystals. Responsive to changes in the distance between the X-ray source and detector, the detector is positioned in a manner to adjust the angle of incidence for reducing the shadow to substantially a minimum amount.

A preferred embodiment of the invention is shown in the attached drawings, wherein:

FIG. 1 pictorially shows the invention used in a CAT scanner which is about to X-ray a rocket motor;

FIGS. 2A and B schematically show top and side views, respectively, of a CAT scanner utilizing the invention;

FIG. 3 shows a cross-section of multiple detector modules butted to form a linear array, taken along line 2—2 of FIG. 4;

FIG. 4 schematically shows a single X-ray detector module; and

Figure 5:
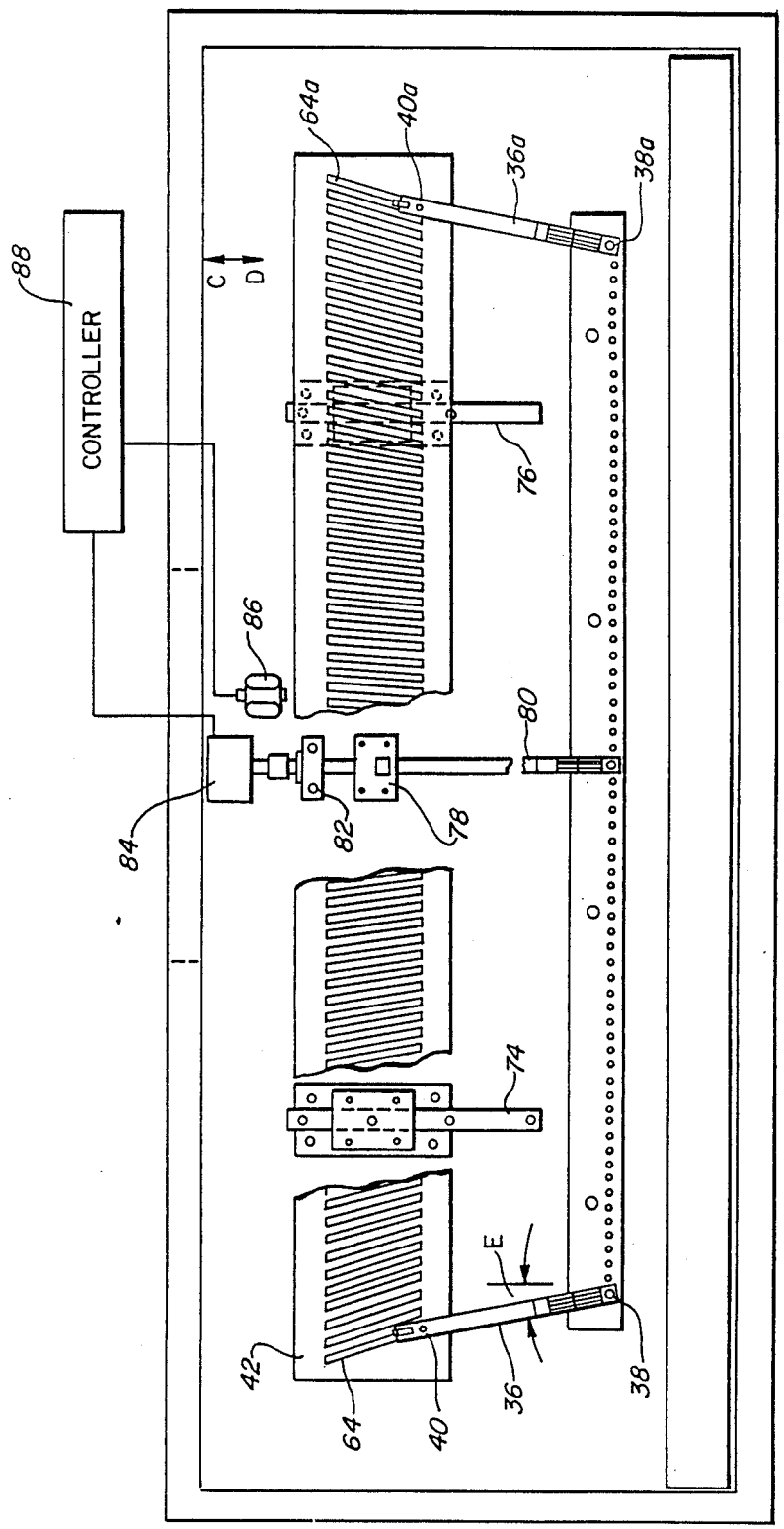

FIG. 5 schematically shows a system for focusing the detector module of FIG. 4.

FIG. 1 pictorially indicates the inventive CAT scanner as it is being used to X-ray a rocket motor. A frame 19 supports a source 20 of X-rays, such as a 150–420 kv tube or a 2 MV linear accelerator, and an opposed X-ray detector 22 for movement to any points in a pair of spaced parallel vertical planes. The object 23 under test (here, a rocket motor) is mounted on a turntable 24 which rotates the rocket motor (see arrows 17) by way of drive motor M7. The turntable 24 is mounted on a carriage which travels linearly over a track 25 by way of drive motor M6. Thus, the rocket motor 23 exposes all of its surfaces to X-rays as it both rotates and travels between the source 20 and the detector 22. A computer responds to the resulting signals from the detector 22 to construct a tomographic X-ray image of object 23.

A number of separate motors M1-M5 drive components mounted on the supporting frame structure 19 to position the X-ray source 20 and the detector 22 relative to the object 23 under test.

The operation of the CAT scanner of FIG. 1 is explained with the help of FIG. 2 in which FIG. 2A is a stylized top view and FIG. 2B is a corresponding side view of the structure shown in FIG. 1. The source 20 of X-rays is displaced from the detector 22 by a source-to-detector distance 26, which may vary. The X-rays tend to spread into a somewhat fan-shaped pattern, as seen at 27. Pre- and post-collimator beam shapers 28, 30 are positioned within the path of the X-rays to reduce the width or thickness of this fan-shaped pattern of X-rays. A pair of plates 32 made from material which is opaque to X-rays form a blinder which defines a slot length 34 through which X-rays may pass in order to illuminate the surface of detector 22, which includes an array of scintillation crystals.

The object 23 under test or study moves past the blinders 32 and across the slot 34 in order to cast a shadow in the X-rays illuminating the scintillating surface of the crystals forming detector 22. They give an output signal in the form of the object under study, which represents the desired X-ray image.

From an inspection of FIG. 2, it is obvious that as the X-ray source-to-detector distance 26 increases or decreases, the base of the conical X-ray beam 27 spreads or contracts within the imaging area, thereby changing the angle of incidence upon the illuminated surface of the detector 22.

The detector crystals are arranged in a plurality of elongated strips 36 which are pivotally connected at one end 38 (FIG. 2B) to the machine and at the other end to a cam follower pin 40. The cam follower pin rides in individually associated cam slots 64 (FIG. 4) formed in a focuser plate 42. As a focusing motor 44 drives the focuser plate 42 back and forth in directions C or D, the cam-controlled end of the strip 36 of detector crystals swings into a position where septa on the strip 36 cast the minimum shadow on the crystal.

FIG. 3 is an enlarged cross-section of an X-ray detector 22, also shown in FIG. 4, which includes a plurality of spaced parallel septa 52 extending forward from the scintillating surfaces 53 of the crystals. An individual scintillation crystal 54 is buried between each pair of the longitudinal septa 52. The septa may have any suitable height, such as an inch or so above the surface 53 of the crystal. Thus, the full surfaces 53 of all of the crystals are maximally illuminated by the X-rays only when the detector is pointed directly toward the source of X-rays. In that way the total effect of all shadows can be minimized.

If the source 20 of X-rays is subsequently moved to any other location relative to the septa, they again cast shadows over some portion of the total crystal surface. Thus, to aim or focus the detector, it is mounted on a mechanical support which pivots or swings about the fixed point 38. More particularly, FIG. 3 shows a corridor width 58 extending linearly from a neighboring septum. When the detector is correctly positioned, this relatively narrow corridor 58 contains both the crystal and the X-ray source located perpendicularly above the crystal. When the X-ray source is properly positioned at the point "Y" within the corridor 58 (for all crystals), the angle of incidence of X-rays illuminating the surfaces 53 of the detector crystals 54 is approximately 90°. On the other hand, if the X-ray source is at point "X", for example, the angle of the incidence is too great and the detector strip 36 should pivot in direction A so that point X falls within the corridor 58. If the X-ray source is at point Z, the incident angle is too great in the opposite direction and the detector 36 should pivot in direction B so that point Z lies within the corridor 58.

FIG. 4 schematically shows an entire detector module 36 which is in the form of an elongated strip, plate, or bar having thereon linearly spaced septa 52, with crystals 54 therebetween, and constructed as shown in FIG. 3. One end of the detector module 36 is pivotally connected at 38, to any suitable stable supporting structure (not shown), such as a table, for example. The opposite end of the strip, plate or bar 36 comprises a cam-follower pin 40 engaging a suitable cam slot 64. Thus, depending upon the location of the source 20 of X-rays, that end of the detector array 36 may swing in either of the directions A or B to orient the septa 52 relative to the source. One way of finding and fixing the position of cam follower pin 40 is to provide a plurality of sensing switches distributed along the path of travel provided by the cam slot 64. Another way is to detect the maximum strength of a signal from the detector module. Still another way is for a microprocessor to memorize certain desirable positions which correspond to the various distances 26 (FIG. 2A) between source 20 and the surface of the detector crystals 54.

The source-to-detector or source-to-image-plane distance 26 (sometimes called "SID") between the source 20 of X-rays and the detector module 36 is of considerable importance. At the close extreme, the source should be as close as possible to the detector in order to give a signal with a maximum strength and a minimum signal-to-noise ratio. At the far extreme, the X-ray beam flares out and this has a magnifying effect upon the size of the image resulting from the X-ray. This magnification can be seen in FIG. 2A where the fan 27 of X-rays becomes larger as the distance 26 increases.

The principles schematically illustrated in FIGS. 2-4 are incorporated into the practical embodiment of FIG. 5 which focuses individual detector modules 36 by means of an individual cam follower pins 40. Each cam follower is dedicated to and fixed in an end of an individually associated detector module 36. Each cam is a continuous slotted path 64 formed in a plate 42, the shape of which is a function of the position of the septa and the location of the scintillating surfaces in a given detector module, relative to the position of the X-ray source 20.

FIG. 5 shows an array of detector modules 36, each constructed as disclosed in FIGS. 3 and 4. There are any suitable number of modules 36 . . . 36a, each of which is individually connected at one end to a frame or "ground" at a pivot point 38 . . . 38a. At its opposite end, each detector module 36 is connected into an individually associated cam slot 64 . . . 64a, by a suitable cam follower pin 40 . . . 40a. There is a separate detector module 36 (not shown) associated with each of the remaining cam slots. The cam slots are all formed in the focuser plate 42 which is mounted to slide back and forth in directions C, D along linear bearings 74, 76. The angles of the cam slots 64 . . . 64a fan out so that the outermost modules 36 . . . 36a swing further than the modules which are between them.

If the focuser plate 42 is in the position shown in FIG. 5 (fully extended in direction C), the detectors 36 ... 36a are at a relatively shallow angle E relative to the perpendicular (i.e. the detector modules 36 ... 36a are the closest that they can come to being parallel to each other).

If the focuser plate 42 is moved as far as possible in direction D, the cam follower pins 40 ... 40a of detectors 36 ... 36a fan outwardly and away from each other (the angle E becomes larger) as is shown by the outward flair of slots 64 ... 64a. Thus, by properly positioning the focuser plate 42, the detectors are all optimally positioned relative to the distance 26 (FIG. 2A) between the X-ray source 20 and the detectors 36.

The outermost detector modules 36, 36a at the left and right extremes of FIG. 5 must rotate the most for a given change in the SID, and the centrally located ones must rotate the least. Accordingly, the cam slots 64 at the leftmost side of plate 42 are angled progressively more to the left as their locations get closer the left end of the plate, and conversely the cam slots at the right side are angled progressively more to the right as their locations get closer to right end of the plate, whereas the center-most slots are angled the least. If one of the modules 36 ... 36a is located dead center relative to the x-ray source, then it need not rotate at all, and needs no cam follower and cam slot.

Attached to the focuser plate 42 is a threaded drive nut 78, through which a lead screw 80 passes. The lead screw is supported by any suitable number of pillow blocks (one of which is seen at 82). A motor 84 is coupled either directly or through a gear train, a timing belt, or the like, to rotate the lead screw 80 and thus to drive the nut 78 and focuser plate 42 back and forth in directions C, D, depending upon the direction of lead screw rotation. Motor 84 may be a stepping motor driven by a computer counting a predetermined number of stepping pulses or an encoder-controlled DC servomotor with closed-loop feedback control.

The position of the focuser plate 42 may be determined by one or more limit switches or proximity sensors, one of which is shown at 86. In a preferred embodiment, the sensor 86 detects when the focuser plate 42 is in a home position. From this home position, the motor 84 is driven to move the focuser plate 42 along linear bearings 74, 76 and thereby to rotate the detectors apart or together. At some point along the excursion C, D, the physical positions of the detectors 36 ... 36a relative to the X-ray source 20 are such that a minimum amount of shadow is cast by the septa upon the scintillation surfaces 53 of crystals 54. At this point, the collective output of the detector array becomes a maximum.

If the motor 84 continues turning the feed screw 80, the detectors 36 ... 36a continue to move. Soon, the septa again begin to cast larger shadows on the crystals and the strength of the signals begin to diminish. Then, a suitable counter or memory in a controller circuit 88 drives the motor backward to where the maximum strength signal occurred; or, the controller can simply hunt for the signal of maximum strength.

Preferably, the cam follower positioning has a maximum tolerance between the cam slots and the cam followers to yield a maximum detector orientation angle error of less than 0.05 degrees.

As an alternative to the use of the hunting or counting type control, a plurality of sensors switches 86 may be located at discrete intervals along the entire excursion route of focuser plate 42. Then, any movement or change in the source-to-detector distance 26 (FIG. 2A) automatically enables an individually associated limit switch 86 which causes the motor to drive the focuser plate 42 to a position corresponding to the position of that enabled switch. Thus, there may be independent, preset focuser plate positions which correspond to specific source-to-detector distances. In still another alternative, a position encoder may be used in connection with a predetermined address for each source-to-detector distance. Then, the motor 84 simply drives the focuser plate 42 to a position corresponding to that address.

This dynamic focusing improves the quality of a digital radiography or computed tomography image by improving X-ray scatter immunity and thus increasing the X-ray signal-to-scatter ratio. At the same time, it increases the versatility of the CAT scanner by permitting variation of the source-to-detector distance, which provides for multiple CAT scanner reconstruction field sizes. Various size objects may then be imaged in the same CAT scanner without sacrificing image quality. The focuser plate/cam concept provides for precise and simultaneous multiple X-ray detector array focusing responsive to operation of a drive motor and to position feedback sensors. The accuracy of the focusing device is a function of the precision of the cam slot array, permitting the detector modules to be positioned to accuracies of less than 1/10th of one degree, relative to the fixed pivot point 38.

Those who are skilled in the art will readily perceive how to modify the invention. Therefore, the appended claims are to be construed to cover all equivalent structures which fall within the scope and spirit of the invention.

We claim:

1. A dynamic focusing device for a penetrating radiation scanner, said device comprising at least one detector means located in a position to receive, be illuminated by, and respond to penetrating radiation; a source of penetrating radiation which is movable toward or away from said detector means; said detector means comprising a plurality of individual detectors, a plurality of septa for separating said individual detectors, said septa extending beyond said individual detectors far enough to reduce lateral penetrating radiation scatter and to cast shadows upon said individual detectors responsive to an illumination thereof from said penetrating radiation source; and means for dynamically orienting said detector means as a function of the changing distance from said detector means to said source of penetrating radiation in order to reduce substantially to a minimum any shadow cast by said septa upon said individual detectors.

2. The device of claim 1 wherein said detector means is in the form of an elongated module carrying a plurality of said septa and individual detectors, said elongated module having a pivot point at one end, and said dynamic orienting means including focuser means for swinging said module about said pivot point in response to movement of said focuser means.

3. The device of claim 2 wherein there are a plurality of said detector means, said focuser means being individually coupled to swing at least one of said modules about said pivot point.

4. The device of claim 3 wherein said focuser means swings said modules to orientations in which all of said individual detectors are focused on said source of penetrating radiation at each of a plurality of distances between said source of penetrating radiation and said detector means.

5. The device of claim 4 wherein said detector means give output signals of different strengths depending upon the orientations to which said modules are swung by said focuser means, means for detecting the maximum of said output signals, and means for causing said focuser means to swing said modules to a point which gives an output signal having a maximum signal strength.

6. The device of claim 4, wherein said detector means travels along an excursion route, said device further comprising a plurality of sensing switches distributed along the excursion route of said detector means for identifying a plurality of orientations to which said modules may move, means for selectively enabling one of said sensing switches corresponding to a distance between said source of penetrating radiation and said detector means, and means for moving said modules means to locations identified by said enabled sensing switch.

7. The device of claim 4 further comprising means for memorizing a plurality of positions of said detector means relative to respective distances between said source of penetrating radiation and said detector means, and means responsive to a change in said distance between said source of penetrating radiation and said detector means for moving said detector means to a memorized orientation corresponding to the new distance of said source of penetrating radiation.

8. A system for dynamically scanning an object under study using penetrating radiation, said system comprising means for directing a penetrating radiation source to illuminate a given area which is remote from said radiation source, detector means for collecting penetrating radiation falling on a surface in said given area, means for producing a shadow on said surface, said shadow-producing means being interposed between said penetrating radiation source and said surface, said shadow increasing or decreasing as a function of the angle of incidence of said penetrating radiation illuminating said surface, means for changing the distance between said penetrating radiation source and said detector means, and means responsive to a change in the distance between said penetrating radiation source and said detector means for, concurrently with said change in distance, orienting said detector means for collecting penetrating radiation in order to adjust said angle of incidence to reduce said shadow to substantially a minimum amount.

9. The system of claim 8 wherein said shadow-producing means is at least one upstanding septum having a height above said surface which is sufficient to control lateral scattering of penetrating radiation illuminating said surface.

10. The system of claim 9 wherein said detector means comprises a plurality of detector devices which are mounted to swing between two limits, and means for adjusting the orientations of said detector devices in order to produce substantially a maximum detector signal strength.

* * * * *